US006688890B2

(12) United States Patent
von Buegner

(10) Patent No.: US 6,688,890 B2
(45) Date of Patent: Feb. 10, 2004

(54) DEVICE, METHOD AND COMPUTER PROGRAM PRODUCT FOR MEASURING A PHYSICAL OR PHYSIOLOGICAL ACTIVITY BY A SUBJECT AND FOR ASSESSING THE PSYCHOSOMATIC STATE OF THE SUBJECT

(75) Inventor: Peter-Raphael von Buegner, München (DE)

(73) Assignee: m-tec AG, Munich (DE)

( * ) Notice: Subject to any disclaimer, the term of this patent is extended or adjusted under 35 U.S.C. 154(b) by 0 days.

(21) Appl. No.: 10/072,193

(22) Filed: Feb. 7, 2002

(65) Prior Publication Data

US 2002/0111744 A1 Aug. 15, 2002

(30) Foreign Application Priority Data

Feb. 9, 2001 (DE) .......................................... 101 05 965

(51) Int. Cl.[7] ................................................. G09B 7/00
(52) U.S. Cl. ...................................... 434/322; 434/362
(58) Field of Search ................................ 434/236, 247, 434/258, 322, 323, 327, 335, 346, 351, 362; 482/1, 3, 4, 5, 6, 7, 8, 9

(56) References Cited

U.S. PATENT DOCUMENTS

| | | | | | |
|---|---|---|---|---|---|
| 4,878,384 A | | 11/1989 | Bruhn | ........................ | 73/379 |
| 4,919,418 A | * | 4/1990 | Miller | ........................ | 482/6 |
| 4,934,694 A | * | 6/1990 | McIntosh | ........................ | 482/9 |
| 5,229,756 A | * | 7/1993 | Kosugi et al. | ........................ | 345/156 |
| 5,308,296 A | * | 5/1994 | Eckstein | ........................ | 482/5 |
| 5,362,069 A | * | 11/1994 | Hall-Tipping | ........................ | 463/7 |
| 5,577,981 A | * | 11/1996 | Jarvik | ........................ | 482/4 |
| 5,725,472 A | * | 3/1998 | Weathers | ........................ | 600/21 |
| 5,911,581 A | * | 6/1999 | Reynolds et al. | ........................ | 434/236 |
| 6,099,319 A | | 8/2000 | Zaltman et al. | ........................ | 434/236 |
| 6,149,586 A | * | 11/2000 | Elkind | ........................ | 600/300 |

* cited by examiner

*Primary Examiner*—Kurt Fernstrom
(74) *Attorney, Agent, or Firm*—Peter F. Corless; Steven M. Jensen; Edwards & Angell, LLP

(57) ABSTRACT

The invention relates to a device and a method, as well as a computer program product, for measuring a physical or physiological activity by a subject and for assessing the psychosomatic state of the subject. The subject is automatically provided with a sequence of different sensory stimuli by means of a stimulus generator controlled by a control means. Electrical signals are then derived from a physical or physiological activity by the subject in response to each sensory stimulus provided, in particular a force of pressure exerted on a letter balance. The electrical signals are compared with a pre-settable index value. On the basis of this, information can be obtained about the psychosomatic state of the subject, in particular about preferences and inclinations.

Figure 2:
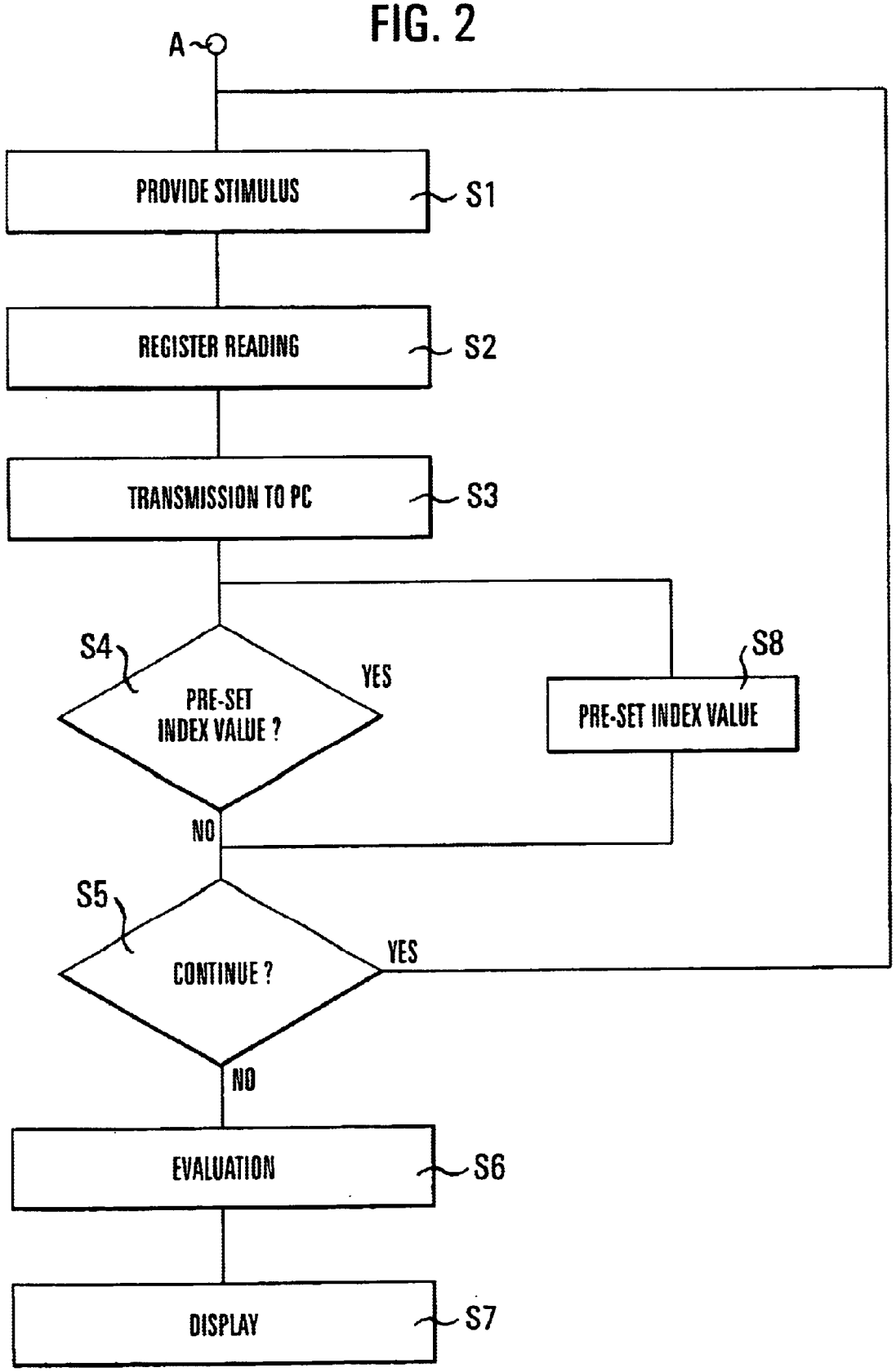

The device is preferably used as an allergy testing apparatus, wherein the sensory stimuli provided in the sequence represent substances which potentially trigger allergies.

23 Claims, 5 Drawing Sheets

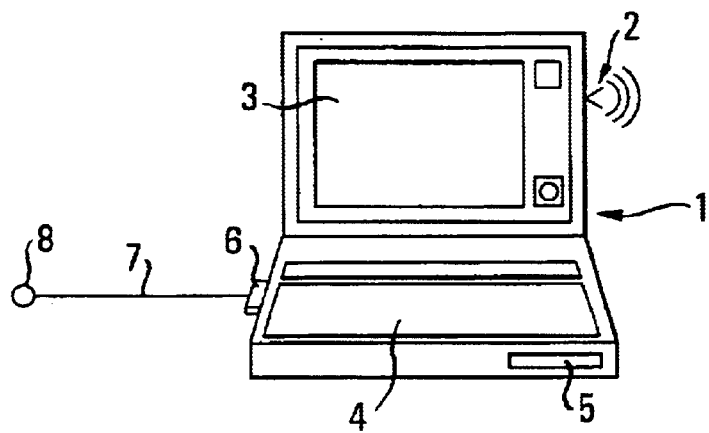
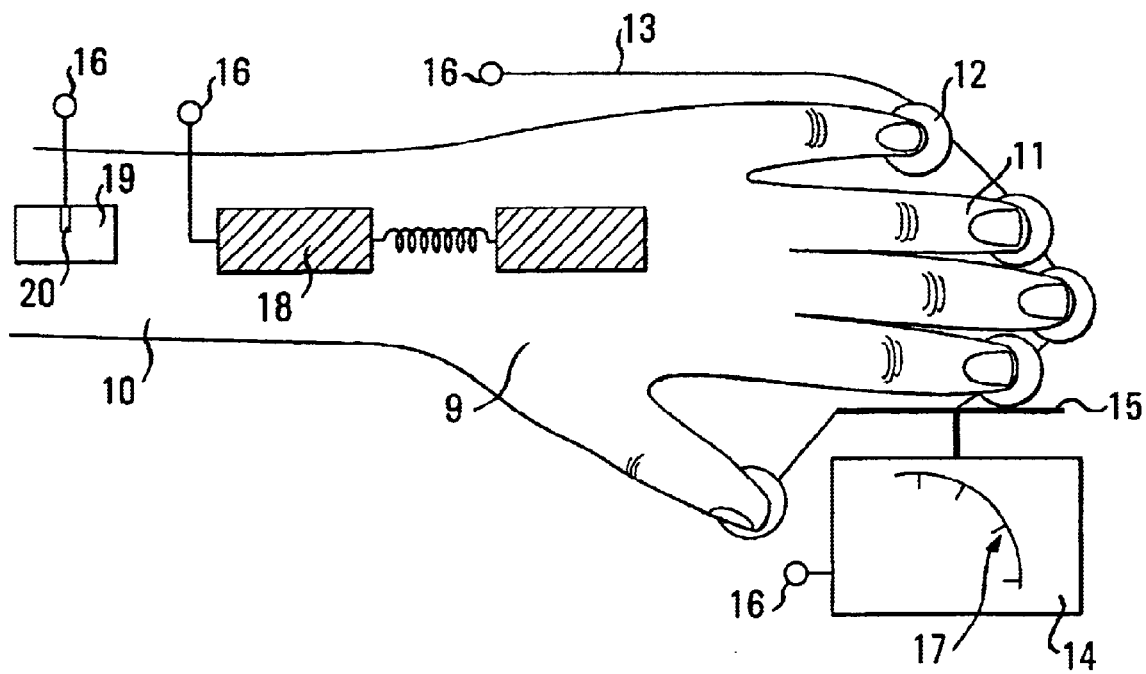
FIG. 1

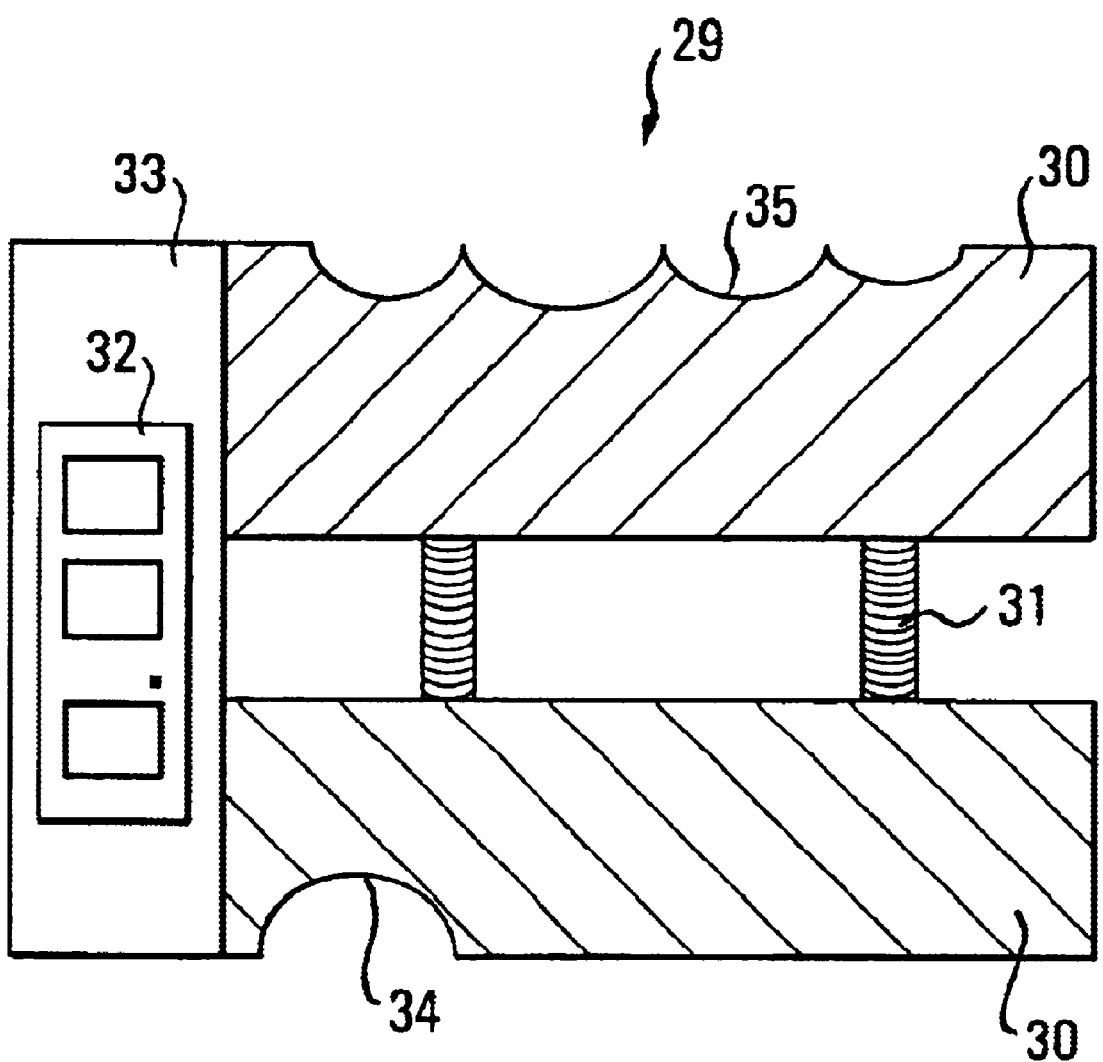

DEVICE, METHOD AND COMPUTER PROGRAM PRODUCT FOR MEASURING A PHYSICAL OR PHYSIOLOGICAL ACTIVITY BY A SUBJECT AND FOR ASSESSING THE PSYCHOSOMATIC STATE OF THE SUBJECT

The present invention relates to a device and a method, as well as a computer program product, for detecting data relating to the psychosomatic state of a subject, in particular for measuring a physical or physiological activity by a subject and for assessing the psychosomatic state of the subject.

Human musculature comprises muscles with transverse and longitudinal strips, which exhibit a tonicity. If a subject is exposed to a sensory stimulus, if for instance they are provided with an image or noise which is linked to positive or negative associations, then tonicity becomes stronger or weaker, according to whether the subject reacts positively or negatively to the sensory stimulus provided. The change in tonicity therefore provides information about the psychosomatic state of the subject.

The method of so-called kinesiology is known in medical diagnosis, in which method a manual muscle test is carried with a subject. Normally, the subject is supposed to try to hold their arm up while another person, for example a physician or therapist, tries to press the outstretched arm down. According to how easy or difficult it is to press the subject's arm down, information is obtained about whether the subject is reacting specifically to what he is being confronted with, or not.

The forces arising have to be subjectively assessed by the physician or therapist. Moreover, the tests in kinesiology are comparatively laborious and time-consuming, since the physician or therapist either has to note the subjectively assessed responses or, when a number of different sensory stimuli are provided, has to note the respective responses intermediately. There thus arises a need for test methods and devices which are more objective and simpler and faster to perform.

The aforementioned tests are also normally comparatively expensive, since a certain diagnosis requires an experienced therapist or physician.

Biofeedback apparatus are known from the prior art, which measure an electrical signal from a physical or physiological activity by a subject, said signal representing for example the subject's current pulse or blood pressure. The signal is electronically processed further and provided to the subject who is then supposed, through feedback, to try to influence the electrical signal and therefore the physical or physiological activity on which it is based. Such apparatus can also be used to improve, through feedback, subjects' stress behaviour.

It is an object of the present invention to provide a device and a method, such that data which can serve as the basis for assessing the psychosomatic state of a subject can be detected for the subject simply and reliably. A computer program product for carrying out the method in accordance with the invention on a computer, as well as a reliable and simple allergy testing apparatus, are also to be provided in accordance with the invention.

A device for detecting data relating to the psychosomatic state of a subject, in particular for measuring a physical or physiological activity by a subject and for assessing the psychosomatic state of the subject, is provided in accordance with the invention, said device comprising a stimulus generator presenting the subject with sensory stimuli, a control means which controls the stimulus generator such that the subject is automatically provided with a sequence of different sensory stimuli, a sensor deriving an electrical signal from a physical or physiological activity by the subject in response to a provided sensory stimulus, and a comparator comparing the electrical signal with a pre-settable index value.

It is an advantage that data which can provide information about the psychosomatic state of a subject can be obtained automatically from the subject. Thus, no physician or therapist is required in accordance with the invention, to obtain such data. Rather, the device can carry out tests on the subject automatically. The data thus obtained can serve as the basis for a subsequent assessment of the psychosomatic state of the subject. However, this does not necessarily require a physician or therapist. It also has the advantage that the data can be obtained faster, since the sensory stimuli are provided automatically. It also has the further advantage that the data are more objective, since they can no longer be distorted by the subjective perception of a physician or therapist. Thus, the data allow a more certain diagnosis in accordance with the invention.

All stimuli which are suited to inducing a physical or physiological activity in the subject can be used as sensory stimuli. Visual stimuli, for example images, colours or texts, acoustic stimuli, for example tones, melodies, noises or spoken sequences of words, and tactile stimuli, for example touch stimuli induced by pressure actuators, are preferably used in accordance with the invention. In principle, however, stimuli may also be used which act on the taste nerves or olfactory nerves of the subject, to which end the stimuli can be induced either in a natural form, for example as an odour, or by means of electrodes applied to a suitable location.

A computer or data processing means is particularly preferably used as the control means, in particular a portable computer which can also simultaneously serve as the stimulus generator for generating the sensory stimuli. A particularly simple and cost-effective device is therefore provided in accordance with the invention.

The electrical signal derived from the sensor is compared with an index value by means of a comparator. This index value can be pre-set in accordance with the invention and is particularly preferably individually adjusted to the activity pattern of the subject. While the sequence of sensory stimuli is being provided, the subject has the task of responding to the sensory stimulus in such a way that the strength of the physical or physiological activity corresponds to the index value. The strength of the response is not shown to the subject. A data set can be derived from the difference between the strength of the detected physical or physiological activity in response to a provided sensory stimulus and the pre-set index value, said data set showing whether the activity in response to the provided sensory has turned out comparatively strong or weak. This information can be used in a subsequent assessing step, to assess the psychosomatic state of the subject. In particular, it can be assessed whether the sensory stimulus has induced a positive or negative response in the subject.

Since the subject is provided not with a single sensory stimulus but rather with a sequence of different sensory stimuli, possible fluctuations in the physical or physiological activity by the subject can be filtered out or averaged out. In particular, repetitions of one and the same sensory stimulus may be contained in the sequence, such that an average can be taken over a number of readings for a physical or physiological activity by the subject in response to one and the same sensory stimulus, in order to obtain an average value for the respective activity. Advantageously, the derived data therefore represent an even better basis for assessing the psychosomatic state.

The control means preferably comprises a data base which contains data sets corresponding to those sensory stimuli to be provided which are to be provided to the subject. The data sets can be combined into a specifically pre-set sequence, however they can also be selected in a control menu by an operator, such that an individual sequence can be produced for each subject. The data base can also be in an electronic form and stored in a data memory, for example on a CD-ROM.

An input device may also be expediently provided, inputting further data sets into the data base which stand for sensory stimuli with which the subject is to be provided. If, for example, the subject is to be provided with texts, then further texts may be inputted into the control means via a keyboard. However, an input/output interface to external stimulus generators, for example tone or tone sequence generators, speech recording apparatus, graphics inputting apparatus and the like, may also serve as an input device.

The sequence of sensory stimuli can run at a specifically pre-set speed or at a variably pre-settable speed, in particular adjusted to the response capacity of the subject. Particularly preferably, however, the control means controls the stimulus generator in such a way that a next stimulus from the sequence of sensory stimuli is only provided once the subject has responded to a preceding stimulus, which is particularly preferably established by the strength of an electrical signal, detected in response to the preceding stimulus and corresponding to the physical or physiological activity by the subject in response to the previously provided sensory stimulus, exceeding a pre-set threshold value. Advantageously, the threshold value avoids the possibility of signal noise or an activity not in response to a sensory stimulus being inadvertently established, detected as an electrical signal, and processed further.

In principle, all types of sensors with which physical or physiological activities by the subject can be monitored are suitable as sensors. Pressure sensors are particularly preferably used in accordance with the invention, for registering forces of pressure when the subject exerts a force onto the pressure sensor. This way of detecting activities by the subject thus copies the approach known from kinesiology. A balance is particularly preferably used as the pressure sensor, in particular a letter balance which can also comprise an A/D converter and an interface for forwarding the detector signals to an evaluation unit. Alternatively or in addition, EEG sensors, EMG sensors or the like can also be used as sensors in accordance with the invention. Conclusions about the psychosomatic state of the subject can similarly be obtained from the activity patterns obtained in this way.

A processor unit, in particular a microprocessor, is preferably provided for editing and forwarding the data obtained, such that the data obtained are graphically edited and may be displayed on a display and/or stored as a data set, in particular on an exchangeable data carrier. The data obtained can thus be analysed even more simply.

An index value unit is preferably provided, for pre-setting the index value which the respective physical or physiological activity by the subject in response to a provided sensory stimulus is supposed to reach, said index value unit comprising a visual display for displaying the strength of the physical or physiological activity by the subject in response to a test sensory stimulus and a visual display for pre-setting an index value. The subject is provided with at least one test sensory stimulus, with the task of responding such that the strength of the measured activity in response to the at least one sensory stimulus reaches the visually displayed index value.

When the sequence of different sensory stimuli is provided to the subject, the subject has the task of responding to each sensory stimulus as equally as possible and with the strength of the pre-set index value. Thus, any difference between the actual strength of the activity and the index value can be ascertained in a particularly simple way.

Since it may happen that the subject grows tired during a sequence, the control means preferably triggers the index value unit every time the difference between the strength of the physical or physiological activity and the index value exceeds a pre-set threshold value a number of times. If the subject happens to respond comparatively strongly or weakly, this does not yet trigger the establishing of a new index value. Advantageously, the method and device in accordance with the invention can simply take into account tiring or an increased level of activity in the subject.

It is known that certain subjects can also respond exactly oppositely. Such subjects are said to be in reverse. Where, for example, in the case of a positive response to a sensory stimulus, a normal subject would respond particularly acutely, subjects in reverse respond exactly oppositely, i.e. relatively weakly. This also applies to the reverse case of a negative response. In order to filter out such subjects in reverse, the control means is preferably configured such that the subject can also be provided with objectively incorrect information, i.e. information for which it is known for certain that it is not true, wherein the strength of the physical or physiological activity in response to the incorrect information is then compared with the previously established index value. If it is established that the subject is a subject in reverse, then the data obtained in accordance with the invention are evaluated exactly oppositely, i.e. data for comparatively weak responses are converted into data for comparatively strong responses, and vice versa.

The control means is preferably linked to a data base, for example a CD-ROM, comprising data sets specific to the subjects, for generating objectively incorrect information, said data base containing objectively incorrect and/or objectively correct information, and the control means then generating the subjectively incorrect information to be provided to the subject from said data sets.

In accordance with a further aspect of the invention, a method is provided for detecting data relating to the psychosomatic state of a subject, in particular for measuring a physical or physiological activity by a subject and for assessing the psychosomatic state of the subject. In said method, the subject is provided with sensory stimuli, and electrical signals are derived from a physical or physiological activity by the subject in response to a provided sensory stimulus, and the electrical signals are compared with a pre-set index value, wherein the sensory stimuli are provided to the subject automatically, in the form of a sequence of different sensory stimuli.

The method in accordance with the invention is not a diagnostic or therapeutic method. Rather, the method in accordance with the invention serves to derive data which serve as the basis for a subsequent evaluation or assessment which does not have to be performed by physicians or therapists.

In accordance with a further aspect of the invention, a computer program product is also provided which comprises sections of program or software code which may be directly loaded into the working memory of a computer or data processing means connected to at least one sensor for detecting electrical signals from a physical or physiological activity by a subject in response to a sensory stimulus, such that the computer performs the method in accordance with the invention.

A particularly preferred application of the device in accordance with the invention, the method in accordance with the invention and the computer program product in accordance with the invention relates to its application in testing for allergies. To this end, the subject is provided with images and/or texts which represent substances to be tested which potentially trigger an allergy in the subject. From the physical or physiological activity in response to the sequence of sensory stimuli provided, conclusions can be drawn about particular allergies, though also about the subject's preferences. If, for example, the subject responds particularly acutely to images or to the words of certain products, then conclusions can be drawn from the data obtained about an allergy to these products. Advantageously, such an allergy test is particularly cheap and can be performed quickly.

Figure 3:
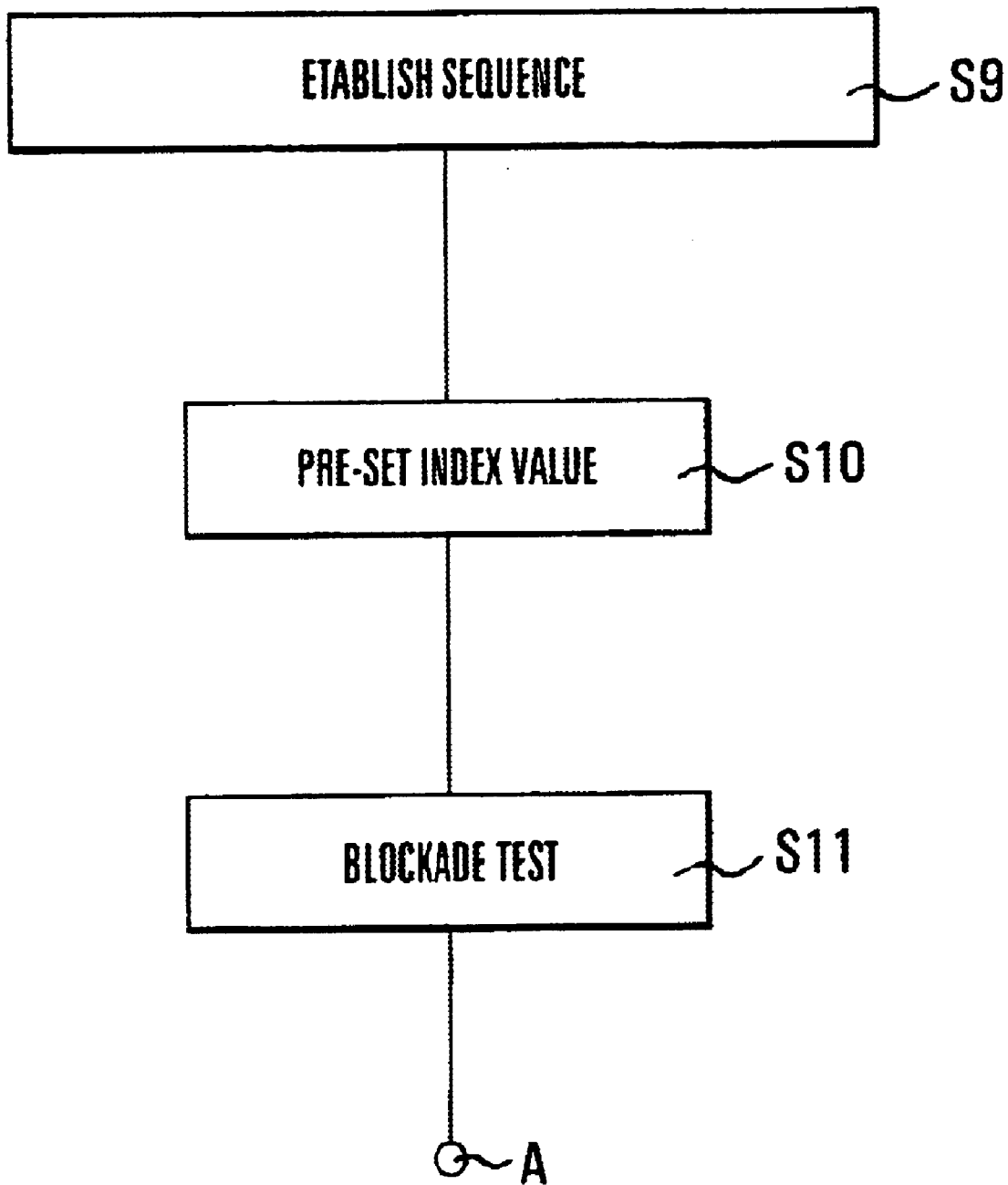
Figure 4:
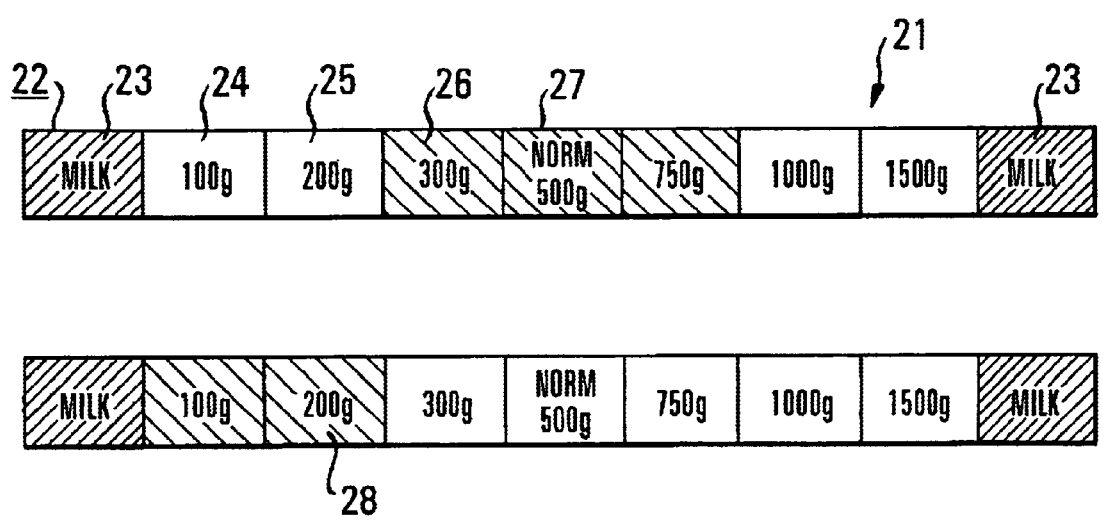

The invention will now be described by way of an example, and referring to the enclosed figures, which show:

FIG. 1 a device in accordance with the invention, comprising a number of example sensors for detecting signals from responses or activities in the area of the subject's hand;

FIG. 2 a schematic flow diagram of a method in accordance with the invention;

FIG. 3 steps of the method which may be performed before the steps of the method according to FIG. 2;

FIG. 4 two examples of possible screen displays, reproducing the response of a subject to the stimulus "milk"; and FIG. 5 a further example of a preferred application of the device in accordance with the invention.

FIG. 1 shows a device in accordance with the invention. It comprises a computer 1 and at least one sensor deriving an electrical signal from a physical or physiological activity by the subject in the area of the hand 9 or forearm 10 in response to a provided sensory stimulus. The computer 1 simultaneously serves as a stimulus generator and a control means. In principle, the stimulus generator and the control means can also form separate units. The computer 1 has a screen 3 for displaying visual stimuli, for example graphics, images or texts, and a speaker 2 for emitting acoustic stimuli, for example tones, noises, melodies or spoken text.

A data base is installed on the computer comprising data sets which represent the sensory stimuli to be provided to the subject, for example data sets for images, graphics, tones, melodies, noises, texts and the like. The data base can be pre-installed and can also contain several types of sequences of sensory stimuli which the operator can select via the keyboard 4 and a menu. The operator can also individually compile the sequence of sensory stimuli to be provided and store it as a data base or file. To this end, the operator individually selects the sensory stimuli to be provided from a menu on the screen 3 via the keyboard 4 or a mouse (not shown). The schematically shown drive 5, for example a drive for a floppy disk, an interchangeable hard-disk or a writable/readable disk, serves to store the compiled sequences.

Once a starting signal has been activated, the computer 1 automatically plays the sequence of sensory stimuli from the data base. Here, the sequence can run at a specifically pre-set speed or at a variable speed, wherein in particular the speed can be adjusted to the response capacity of the respective subject. It can also be provided that a next stimulus from the sequence is only provided once the subject's response to the preceding stimulus has exceeded a pre-set threshold value. To this end, the software of the computer 1 contains a discriminator routine for evaluating the electrical signals detected.

The computer 1 further comprises an interface 6 via which analogue or digital readings from the sensors can be inputted into the computer 1. The cable connections 16 of the sensors are connected to the cable end 8 of the connection cable connected to the interface 6 of the computer 1.

The lower part of FIG. 1 shows a human hand 9 comprising fingers 11 and a forearm 10. An example selection of different sensors is shown, which can serve to derive electrical signals from a physical or physiological activity by the subject. To this end, pressure sensors 12 are arranged under the fingertips. While the sequence is being provided, the subject can be set the task of pressing on the pressure sensors 12 with as constant a force as possible. The pressure sensors 12 are connected to each other via the cable 13, but can also be individually connected to the cable connection 8 of the cable 7 via respective cable connections 16, for transmitting the electrical signals, by wire or wirelessly, to the interface 6 of the computer 1.

A letter balance 14 is shown schematically underneath the hand 9, comprising a balance surface 15 (which serves as a pressure transducer or register) and a scale 17 which should not be visible to the subject while the sequence of sensory stimuli is running. The balance 14 transmits the data, by wire or wirelessly, to the computer 1. To this end, an interface 16 can be provided, in particular an RS 232 or USB interface, which is connected to the interface 6 of the computer 1. While the sequence of sensory stimuli is running, the subject has the task of pressing on the balance 14 with as constant a force as possible in response to each sensory stimulus, according to the index value pre-set in steps S8 or S10 of the method.

Instead of the pressure sensors 12, 14, 15, or in addition to these, other sensors can be provided in the area of the subject's hand 9, forearm 10 or other parts of the body, for example the thigh. Merely by way of example, a goniometer 18 is additionally shown in the area of the wrist in FIG. 1, which measures the angular difference between the wrist and a neutral position in two directions which are perpendicular to each other, and transmits this difference to the computer via the interface 16 and the interface 6. An EMG sensor 19, 20 can additionally be placed on the surface of the skin, which measures the electrical activity induced by a muscle. Moreover, EMG sensors (not shown) can be arranged on various parts of the body, said sensors measuring nerve impulse patterns and transmitting these to the computer 1.

A software is installed on the computer 1 which performs the steps of the method described in the following by way of FIGS. 2 to 4.

FIG. 2 shows an example flow diagram for performing a method in accordance with the invention. In the loop comprising steps S1 to S5 of the method, the subject is provided with a sequence of different sensory stimuli. The loop includes step S1 of the method, in which a sensory stimulus is provided with the aid of a stimulus generator, in particular in the form of a computer. In step S2 of the method, an electrical signal from a physical or physiological activity by the subject in response to the sensory stimulus provided in step S1 of the method is measured by means of the sensors indicated by way of example in FIG. 1. In step S3 of the method, the electrical signal is then transmitted in analogue or digital form to the computer 1. There, the electrical signals are then evaluated in step S6 of the method, and the data obtained are edited and displayed in step S7 of the method.

The loop consisting of steps S1 to S5 of the method runs until the end of the sequence. Then, there is an enquiry in step S5 of the method as to whether the end of the sequence has already been reached or not. If the end of the sequence has not already been reached, the method returns to step S1 of the method.

Evaluation can be performed while the sequence of sensory stimuli is still running. In particular, it can be established in step S4 of the method to what extent the strength of the derived electrical signal differs from the pre-set index value. If the difference between the strength of the electrical signal and the pre-set index value exceeds a threshold value, the method switches to step S8 of the method, in which a new index value is pre-set or the subject is again trained to reach the previous index value, as will be subsequently described by way of step S10 of the method. Following step S8 of the method, the method then returns to the loop S1 to S5.

The subject is thus provided with a sequence of different sensory stimuli. Repetitions can also arise in the sequence at regular or irregular, in particular random, intervals. The subject then has the task of responding to each sensory stimulus with a previously pre-set strength. The subject can, for example, be given the task of pressing on the letter balance 14 shown in FIG. 1 or on the finger pressure sensors 12 with a force of pressure of, for example, about 500 g in response to each sensory stimulus. The subject is given the opportunity beforehand of feeling how strong the index force of pressure of 500 g is, as will be subsequently described by way of step S10 of the method.

While the sequence of sensory stimuli is running, the subject has no opportunity to establish, with the aid of a measuring device, measuring display or the like, how strong the response actually is. Rather, the computer 1 measures how strongly each actual response differs from the index value, for example how strongly the actual force of pressure differs from the index force of pressure. If, for example, the subject responds specifically to a sensory stimulus, then the response usually turns out stronger than when the subject responds negatively to a sensory stimulus. Using the sequence described, a data set can automatically be obtained which provides information about how the subject responds to certain sensory stimuli, and which can provide information about the psychosomatic state of the subject.

The opening step S9 of the method is designed to establish the sequence of sensory stimuli. The sequence can be specifically pre-set, such that operator can trigger the sequence by pressing a start button. The operator can also select from a number of different sequences. To this end, the operator can select a sequence in a data base with the aid of the keyboard 4 and a mouse (not shown), for which purpose a menu control system can be provided on the screen 3. The operator can also select the sequence individually, for example according to the subject. In this respect, symbols for respective test stimuli may be displayed to the operator on the screen 3, for example a textual description, an image or the like. With the aid of the keyboard 4 and a mouse (not shown), the operator can select these symbols and individually combine them into a sequence. The selected sequence is then stored in the working memory of the computer 1 or on a data carrier.

When establishing the sequence in step S9 of the method, the operator can also pre-set whether the sequence is to run at a fixed speed or at a variable speed. The operator can also pre-set a threshold value which the strength of each detected electrical signal must exceed, before a next sensory stimulus from the sequence of sensory stimuli is provided.

Before the sequence is provided to the subject, an index value for the strength of the physical or physiological activity should be pre-set for the subject, or the subject should be trained to reach said index value. To this end, the strength of the current physical or physiological activity is displayed visually on the screen 3 of the computer 1 in the opening step S10 of the method. If, for example, the subject is supposed to press on the pressure sensors shown in FIG. 1, then the force of pressure exerted is displayed on the screen 3 of the computer 1, for example in the form of a pointer or a dot which shows the current force of pressure on a scale. Moreover, an index value which the strength of the physical or physiological activity by the subject to be measured in response to a sensory stimulus is supposed to reach is also displayed in a comparable way in step S10 of the method. If, for example, the subject is supposed to press on a pressure sensor with a force of pressure of about 500 g in response to a sensory stimulus, then a scale may be displayed on the screen 3 such as is shown in FIG. 4, with shading in the area of the index value (500 g).

In step S10 of the method, the subject then exerts the physical or physiological activity to be measured a number of times. For example, the subject is supposed to press on the pressure sensor a number of times with a force of pressure of 500 g (=the index force of pressure) and get used to the feeling of pressing with this index force of pressure.

The display 17 in the letter balance 14 shown in FIG. 1 can also directly serve the purpose of getting used to said index value. In this case, the subject must be forced to not look at the scale 17 while the sequence is running. The scale 17 of the letter balance 14 can also be covered automatically while the sequence is performed.

Once the steps S9 to S11 of the method have been run through, the method switches to step S1 in accordance with FIG. 2.

Step S10 of the method, for training the subject to a pre-set index value, can also be performed while the sequence is provided (step S8 of the method).

It is known that patients can be in reverse. Such persons respond atypically to stimuli. Where, for example, subjects usually respond more strongly to positive stimuli and more weakly to negative stimuli, this is exactly the other way round with subjects in reverse, i.e. they react more weakly to positive stimuli and more strongly to negative stimuli. For persons in reverse, the test method described above would provide incorrect results.

In order to filter out subjects in reverse, step S11 of the method in accordance with FIG. 3 can be performed before steps S1 to S7 of the method in accordance with FIG. 2 are performed, and following steps S9 and S10 of the method.

If the subject has thus been got used to performing the physical or physiological activity to be measured with a pre-set strength in step S10, for example pressing on a pressure sensor with a pre-set force of pressure, then in step S11 of the method, objectively incorrect information is then deliberately provided to the subject, and it is ascertained whether the subject responds more strongly or more weakly to such objectively incorrect information. If the subject responds more strongly to objectively incorrect information, then he or she is a subject in reverse. This test can be carried out a number of times, in order to be able to assess the reverse method more objectively.

In order to generate objectively incorrect information, the computer 1 can be linked to a data base with data sets specific to the subject. This data base can contain objectively correct information, for example verifiable personal details, for example surname, first name, date of birth, significant dates in the subject's life, illnesses, etc. The computer 1 then generates objectively incorrect information on the basis of this objectively correct information. In this respect, it can be provided that the computer 1 generates sets and displays them on the screen 3. To form these sets, the objectively correct information contained in the data base specific to the subject is altered in such a way that the information is objectively incorrect. For example, the subject's first name can be changed to another first name, which is therefore objectively incorrect. The subject is then shown a set formed using this incorrect first name, and the subject's response to this objectively incorrect set is ascertained.

All the subject's details can be used to generate this objectively incorrect information. Instead of the data base specific to the subject containing objectively correct information, it can even also contain objectively incorrect information which can be inputted either by the subject themselves or by a third person informed with the objectively correct information regarding the subject. If the data base specific to the subject already contains objectively incorrect information, the computer 1 does not need to distort information taken from this data base in order to generate objectively incorrect information, but can rather take it on directly.

In a further embodiment, it can be provided that the reverse test in accordance with step S11 of the method is also always performed following a new pre-setting of the index value (step S8 of the method) in the loop S1 to S5, when it is thus established in step S4 of the method, by way of the ascertained physical or physiological activity by the subject in response to a provided sensory stimulus, that a new index value is to be pre-set.

The aforementioned reverse test can also be used to filter out so-called blocked subjects, who are blocked i.e. show no preferably positive or negative response. To this end, the subject is provided with objectively incorrect information, as described previously. If it is established that the subject does not respond more strongly or more weakly but always the same, then the device in accordance with the invention can establish that the subject is blocked. In such a case, a warning indication can be displayed on the screen 3 of the computer 1 and/or the method in accordance with the invention can be aborted.

FIG. 4 shows an example of a graphic evaluation of a subject's response to the sensory stimulus "milk", which can be provided for example as spoken text, as an image or as text on the screen 3 of the computer 1. FIG. 4 is based on the fact that the subject is supposed to press on a pressure sensor with an index force of pressure of 500 g.

In accordance with FIG. 4, the display 21 comprises a field 22 in which the provided sensory stimulus 23 is schematically shown, for example as a word or image. The display 21 also comprises a number of fields 24 with a display 25 for the strength of the force of pressure corresponding to the respective field 24, the values of the displays 25 in FIG. 4 increasing from left to right from 100 g to 1500 g.

The upper part of FIG. 4 is based on the fact that the subject has responded to the stimulus "milk" a number of times with a force of pressure in the range 300 g to 750 g, i.e. more strongly and more weakly in approximately equal distribution. The display 21 converts this information into a neutral display in which the range around the index force of pressure of 500 g is backed in colour or shaded, symmetrical about the index force of pressure, such that it can be recognised from a glance at the display 21 that there is no particular reference in the subject's response.

The lower part of FIG. 4 is based on the fact that the subject has responded a number of times to the stimulus "milk" with a force of pressure of 100 g to 200 g, i.e. too weakly. In this case, the fields 24 with the strengths 100 g and 200 g are backed in colour (28). Preferably, a different colour is chosen in this case than in the upper part of FIG. 4, for example red in the lower part and green in the upper part. It can therefore be recognised from a glance at the display 21 that the subject in the upper case responded neutrally, and in the lower case with a preference towards weaker forces of pressure, which may indicate a pathological difference, for example that the person feels insecure with the stimulus "milk", or even responds allergically.

In addition to the coloured background, it can also be provided that, every time the subject has responded with a strength corresponding to the strength of a field 24, a black dot or a similar symbol is displayed in the respective field 24, such that additional information about the subject's preferences can be obtained from the accumulation of dots.

A particularly preferred application of the device and the method in accordance with the invention relates to an allergy test in which the subject is provided with a sequence of visual and/or acoustic stimuli and/or texts, and the subject's response to each sensory stimulus is ascertained, for example when the subject presses on the letter balance 14. From the difference between the force of pressure exerted and the index force of pressure 27, it can be simply ascertained for each "provided" test substance, whether the subject responds insecurely or not. This can permit conclusions about the presence of the possible allergy to the respective substance, without the subject actually having to be physically exposed to the substance potentially triggering an allergy.

Particularly advantageously, the present invention can be realised by a combination of a commercially common computer, in particular a laptop, and a letter balance which has an interface, for example an RS 232 interface, in order that the computer reads the readings of the letter balance. Given this combination, one can fall back on commercially common components and software products.

The computer program product in accordance with the invention comprises sections of program code or software code which each perform one of the steps of the method described above, such that the method in accordance with the invention can be performed when the computer program product or software is loaded into the working memory of a commercially common computer, preferably a laptop, or more generally of a data processing means.

FIG. 5 shows another example of a preferred application of the device in accordance with the invention. In this application, the data processing means is preferably integrated into the device 29 and is therefore not shown. Essentially, the device 29 shown in FIG. 5 corresponds to a hand muscle testing apparatus in the fashion of conventional hand muscle training apparatus. In accordance with FIG. 5, the device 29 measures the force with which the two blocks 30 of the device 29 are pressed together. To this end, the device 29 comprises two opposing blocks 30 with indentations 35 for the index finger to the little finger and an indentation for the thumb. The two blocks 30 are connected to each other via the sections 31. The sections 31 can comprise restoring means, for example springs, which restore the blocks 30 to the resting position shown in FIG. 5. The sections 31 can also be rigid sections, wherein a pressure register or transducer (not shown) is provided on at least one front face, said pressure register measuring the strength of the force with which the subject presses the blocks together. A section 33 is situated on the front face which is only connected to one block. The other block can be arranged at a distance from this section or slidable in it. A display 32, for example an LCD display, is situated in the section 33. The data processing means not shown is integrated into the section 33. The data processing means receives the signals measured by the pressure or force registers (not shown) which represent the strength with which the two blocks 30 are pressed together by the subject. The data processing means is configured to perform the steps of the method cited above.

A particularly preferred application is as follows: the device 29 is suitable as a mobile test device, for example for testing whether a product should be bought by the subject or not or for making other decisions. Before the subject has to make the decision, he or she presses the clamp blocks together a few times, for example two to at most ten times, with the aim of pressing the clamp blocks together with a constant force. In this way, an index value is provided for the device 29.

The subject then presses the two clamp blocks together every time a decision has to be made, wherein the pressure or force registers not shown measure the forces arising from this and forward these to the data processing means not shown. By comparison with the previously ascertained index value, the data processing means can then establish whether the strength of the force or pressure is greater or smaller than the previously ascertained index value. The result is displayed on the display 32. Alternatively, just the strengths measured can be displayed on the display 32. The subject can read from this whether the decision should actually be made or not. Thus, the device 29 manages without a stimulus generator. The sensory stimuli are rather provided by the environment.

A greatly preferred application of the device in accordance with FIG. 5 is a shopping test apparatus which is supposed to assist the subject when making purchase decisions.

What is claimed is:

1. A device for measuring a physical or physiological activity by a subject and for assessing the psychosomatic state of said subject, comprising:
   a stimulus generator presenting the subject with sensory stimuli;
   a control means for controlling the stimulus generator such that the subject is automatically provided with a sequence of different sensory stimuli;
   a pressure sensor deriving an electrical signal from a physical or physiological activity of the subject in response to a provided sensory stimulus; and
   a comparator, for comparing a strength of the electrical signal with a pre-settable index value.

2. The device as set forth in claim 1, wherein the control means comprises a data base containing data sets for a sequence of specifically pre-set acoustic and/or visual stimuli and/or texts which are provided to the subject.

3. The device as set forth in claim 2, further comprising an input device for inputting data sets into the data base, each representing a sensory stimulus of the sequence.

4. The device as set forth in claim 1, wherein the control means causes the stimulus generator to make the sequence run at a specifically pre-set or variably pre-settable speed.

5. The device as set forth in claim 1, wherein the control means controls the stimulus generator such that a next stimulus from the sequence of sensory stimuli is only provided once the strength of an electrical signal detected in response to the preceding stimulus exceeds a pre-set threshold value.

6. The device as set forth in claim 1, wherein the pressure sensor is a letter balance or a hand muscle testing apparatus, and an A/D converter converts the detected electrical signals into digital signals.

7. The device as set forth in claim 1, wherein a processor unit is provided for editing the digital signals graphically and/or storing them as a data set.

8. The device as set forth in claim 1, further comprising an index value unit which comprises a visual display for displaying the strength of the physical or physiological activity by the subject in response to a sensory stimulus, and a visual display for pre-setting an index value which the strength of a physical or physiological activity by the subject in response to a sensory stimulus is to reach.

9. The device as set forth in claim 8, wherein the control means triggers the index value unit every time the difference between the strength of the physical activity and the index value exceeds a pre-set threshold value a number of times.

10. The device as set forth in claim 9, wherein the control means is configured to present the subject with objectively incorrect information and to compare the strength of the physical or physiological activity in response to the objectively incorrect information with the threshold value.

11. The device as set forth in claim 10, wherein the control means is linked to a data base comprising data sets specific to the subject, such that the objectively incorrect information is derived from said data base.

12. A method for measuring a physical or physiological activity by a subject and for assessing the psychosomatic state of the subject, wherein:
   the subject is provided with sensory stimuli; and
   electrical signals are derived from a physical or physiological activity by the subject pressing a pressure sensor in response to a provided sensory stimulus, and a strength of each electrical signal is compared with a pre-settable index value, wherein
   the sensory stimuli are automatically provided to the subject in the form of a sequence of different sensory stimuli.

13. The method as set forth in claim 12, wherein the sequence comprises acoustic and/or visual sensory stimuli and/or text, which are specifically pre-set or individually inputted into a data base for the subject.

14. The method as set forth in claim 12, wherein the sequence of sensory stimuli runs at a constant speed or at a pre-settably variable speed.

15. The method as set forth in claim 12, wherein a next stimulus from the sequence of sensory stimuli is only provided once the strength of an electrical signal detected in response to a preceding stimulus exceeds a pre-set threshold value.

16. The method as set forth in claim 12, wherein the pressure sensor used to measure the pressing force exerted by the subject is a letter balance or a hand muscle testing apparatus.

17. The method as set forth in claim 12, wherein electrical signals, detected while a sensory stimulus is provided and/or in a pre-determined time interval after a sensory stimulus has been provided, are digitised and stored in an intermediate memory.

18. The method as set forth in claim 12, wherein the digital signals are graphically edited and/or stored as a data set.

19. The method as set forth in claim 12, wherein the step of comparing the strength of each electrical signal to the pre-settable index value is preformed every time the difference between the strength of the physical or physiological activity and the index value for the strength of the physical or physiological activity is visually displayed.

20. The method as set forth in claim 12, wherein the step of comparing the strength of each electrical signal to the pre-settable index value is preformed every time the difference between the strength of the physical or physiological activity and the index value exceeds a pre-set threshold value a number of times.

21. The method as set forth in claim 12, wherein the subject is firstly provided with objectively incorrect information, and the strength of the physical or physiological activity in response to the objectively incorrect information is detected.

22. The method as set forth in claim 21, wherein the objectively incorrect information is derived from a data base of data sets specific to the subject.

23. The device as set forth in claim 1, wherein the device is used to test allergies in the subject.

* * * * *